US006840910B2

(12) United States Patent
Skover

(10) Patent No.: US 6,840,910 B2
(45) Date of Patent: *Jan. 11, 2005

(54) METHOD OF DISTRIBUTING SKIN CARE PRODUCTS

(75) Inventor: Gregory Skover, Princeton, NJ (US)

(73) Assignee: Johnson & Johnson Consumer Companies, Inc., Skillman, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/920,593

(22) Filed: Aug. 1, 2001

(65) Prior Publication Data

US 2003/0120179 A1 Jun. 26, 2003

(51) Int. Cl.$^7$ .......................... A61B 5/00; A61M 35/00
(52) U.S. Cl. ........................ 600/573; 600/306; 604/290
(58) Field of Search .............................. 600/573, 306, 600/309, 310, 314, 362, 346; 604/19, 289, 290

(56) References Cited

U.S. PATENT DOCUMENTS

| | | | |
|---|---|---|---|
| 4,775,361 A | 10/1988 | Jacques et al. | |
| 4,863,970 A | 9/1989 | Patel et al. | |
| 5,155,992 A | 10/1992 | Follensbee et al. | |
| 5,250,023 A | 10/1993 | Lee et al. | |
| 5,445,611 A | 8/1995 | Eppstein et al. | |
| 5,843,114 A | 12/1998 | Jang | |
| 5,885,211 A | 3/1999 | Eppstein et al. | |
| 6,022,316 A | 2/2000 | Eppstein et al. | |
| 6,027,496 A | 2/2000 | Loomis et al. | |
| 6,056,738 A | 5/2000 | Marchitto et al. | |
| 6,155,992 A | 12/2000 | Henning et al. | |
| 6,173,202 B1 | 1/2001 | Eppstein | |
| 2003/0078518 A1 * | 4/2003 | Skover | 600/584 |
| 2003/0083558 A1 * | 5/2003 | Skover | 600/306 |

FOREIGN PATENT DOCUMENTS

| | | |
|---|---|---|
| DE | 43 13 258 A1 | 10/1994 |
| DE | 101 00 127 A1 | 10/2002 |
| EP | 1 098 589 A1 | 5/2001 |
| GB | 2 358 706 | 8/2001 |
| JP | 2001/187205 | 7/2001 |
| WO | WO 97/04832 | 2/1997 |
| WO | WO 97/07734 | 3/1997 |
| WO | WO 97/08987 | 3/1997 |
| WO | WO 97/10745 | 3/1997 |
| WO | WO 97/42882 | 11/1997 |
| WO | WO 97/42888 | 11/1997 |
| WO | WO 97/48440 | 12/1997 |
| WO | WO 98/00193 | 1/1998 |
| WO | WO 98/11937 | 3/1998 |
| WO | WO 99/07277 | 2/1999 |
| WO | WO 99/20181 | 4/1999 |
| WO | WO 99/27852 | 6/1999 |
| WO | WO 99/40848 | 8/1999 |
| WO | WO 99/44507 | 9/1999 |
| WO | WO 99/44637 | 9/1999 |
| WO | WO 99/44638 | 9/1999 |
| WO | WO 99/44678 | 9/1999 |
| WO | WO 00/03758 | 1/2000 |
| WO | WO 00/04821 | 2/2000 |
| WO | WO 00/10579 | 3/2000 |
| WO | WO 00/15102 | 3/2000 |
| WO | WO 00/15188 | 3/2000 |
| WO | WO 00/35530 | 6/2000 |
| WO | WO 00/54920 | 9/2000 |
| WO | WO 00/59373 | 10/2000 |
| WO | WO 00/74763 | 12/2000 |
| WO | WO 00/74764 | 12/2000 |
| WO | WO 00/74766 | 12/2000 |
| WO | 2000/352566 | 12/2000 |
| WO | WO 01/13989 A1 | 3/2001 |
| WO | WO 01/28423 A2 | 4/2001 |
| WO | WO 02/082093 A2 | 10/2002 |
| WO | WO 02/095358 A3 | 11/2002 |

OTHER PUBLICATIONS

Rajadhyaksha et al, Oxazolidinones: Optimizing Delivery of Active Ingredients in Skin Care Products, Mar. 1996, Drug & Cosmetic Industry, vol. 158, No. 3, p. 36.*

Wilson, R., Antioxidants to Augment the Efficacy of Sunscreens, Aug. 1992, Drug & Cosmetic Industry, vol. 151, No. 2, p. 32.*

Badcock, N.R. et al., "The Pharmacokinetics of Ketoconazole after Chronic Administration in Adults", *Eur J. Clin Pharmacol*, 1987, 33, 531–534.

Bork, K. et al., "Histamine Levels in Interstitial Fluid of Lesional and Perilesional Skin in Patients with Chronic Idiopathic Urticaria", *Arch Dermatol Res.*, 1979, 266, 269–276.

Svedman, *Pharm. Res.*, 1988, 15(6), 883–888.

Henry, et al., "Microfabricated Microneedles: A Novel Approach to Transdermal Drug Delivery", *Journal of Pharmaceutical Sciences*, 1988, 87(8), 922–925.

Krogstad, A.L. et al., "Microdialysis methodology for the measurement of dermal interstitial fluid in humans" *British Journal of Dermatology*, 1996, 134(6), 1005–1012.

"Laboratory Procedures Used by the Clinical Chemistry Division, Centers for Disease Control, for the Second Health and Nutrition Examination Survey" (*Hanes II*) *1976–1980*, USDHS, Public Health Services, IV., Analytical Methods, Vitamin C, Atlanta, Ga.

(List continued on next page.)

Primary Examiner—Max F. Hindenburg
Assistant Examiner—David J. McCrosky

(57) ABSTRACT

The present invention relates to a method of distributing a skin care product to a subject, the method including the steps of: (a) obtaining a sample of interstitial fluid from the skin of the subject; (b) measuring the amount of a skin analyte in the sample; and (c) distributing a skin care product to the subject to alter the amount of the skin analyte in the skin of the subject.

25 Claims, No Drawings

OTHER PUBLICATIONS

Maile, L.A. et al., "Active and Inhibitory Components of the Insulin–Like Growth Factor Binding Protein–3 Protease System in Adult Serum, Interstital, and Synovial Fluid", *Endrocrinology*, 1998, 139(12), 4772–4781, XP–002230077.

Service, F.J. et al., "Dermal Interstitial Glucose as an Indicator of Ambient Glycemia", *Diabetes Care*, 1997, 20(9), 1426–1429.

Svedman, P. et al., "Skin Mini–Erosion Sampling Technique: Feasibility Study with Regard to Serial Glucose Measurement", *Pharmaceutical Research*, 1998, 15(6), 883–888.

Tope, W.D., "Multi–Electrode Radio Frequency Resurfacing of Ex Vivo Human Skin", *Dermatol Surg*, 1999, 25, 348–352.

Vaillant, et al., *Eur. J. Clin. Pharmacol*, 1987, 33(5), 529–530.

Zimmerli, W. et al., "Pharmacokinetics of Cefetamet in Plasma and Skin Blister Fluid", *Antimicrobial Agents and Chemotheraphy*, 1996, 40(1), 102–104.

Gabor, "Sensors in Biomedical Applications", *Technomic Pub Co.*, 2000, 223–306.

International Cosmetic Ingredient Dictionary and Handbook, 1997, 7th Edition(2), 1650–1667, 1626.

Liron, et al., "Novel Approaches in Biosensors and Rapid Diagnostic Assays", *Plenum Pub Corp.*, 2000.

Laboratory Procedures used by the Clinical Chemistry Division, Centers for Disease Control, for the Second health and Nutrition Examination Survey (HANESII), *U.S. Dept of Health and Human Services, Public Health Services, Atlanta. Georgia*, 1979, 17–19, 69.

U.S. Appl. No. 09/920,136, Skover.

U.S. Appl. No. 09/920,266, Skover.

* cited by examiner

METHOD OF DISTRIBUTING SKIN CARE PRODUCTS

FIELD OF THE INVENTION

The present invention relates to a method of distributing a skin care product to a subject.

BACKGROUND OF THE INVENTION

Dermal interstitial fluid is a clear, water-like fluid present between the cells in the living skin tissues (i.e., epidermis and dermis) under the stratum corneum. The composition of the interstitial fluid is substantially free of blood cells, but does contain small molecules and proteins. Interstitial fluid both transports nutrients (e.g., glucose) from the blood to the skin cells and removes cellular metabolic wastes (e.g., urea) from the skin cells to the blood. Various components of the interstitial fluid are in equilibrium with living cells in both the epidermis and dermis as well as macromolecular structures located in the subcutaneous tissue.

The correlation of certain endogenous chemicals between the blood and interstitial fluid has been well established. For example, Service et al. used a novel minimally invasive technique to sample minuscule amounts (0.5 microliter) of the interstitial fluid from both healthy volunteers and diabetic patients. See Service et al., Diabetes Care, 20: 9, 1426–9 (1997). Service et al. assessed the accuracy of the glucose concentrations in the interstitial fluid in predicting concurrently measured venous plasma and capillary plasma glucose concentrations. Service et al. concluded that interstitial fluid sampling was a bloodless, minimally invasive technique that provided a medium for glucose measurement, the concentrations of which closely reflected ambient glycemia to a degree comparable with that of capillary glucose measurements. A similar conclusion was also drawn by Krogstad et al., British Journal of Dermatology, 134:6, 1005–12 (1996).

Others have also studied the concentration changes of certain drugs in the interstitial fluid following oral administration. See, e.g., Zimmerli et al., Antimicrobia. Agents. Chemother, 40:1, 102–4 (1996) and Vaillant et al., Eur. J. Clin. Pharmcol. 33:5, 529–30, (1987).

Although sampling interstitial fluid by minimally invasive techniques for diagnostic applications to monitor diseases such as diabetes is known, Applicant has found that certain endogenous substances present in the skin tissues (such as vitamin C) are at a different concentration in the interstitial fluid than in serum. Thus, analysis of substances in the serum is not indicative of the corresponding concentration levels of such substances in the skin. Also, Applicant has also found that the concentration of certain endogenous substance in the interstitial fluid varies as a result of diet, aging, or the effect of external aggressions. Applicant has discovered that the determination of the concentration of certain endogenous substances present in the interstitial fluid, thus, can be used to assess the health of a subjects skin, permitting the administration of cosmetic or pharmaceutical agents to specifically treat the needs of the subject's skin.

SUMMARY OF THE INVENTION

In one aspect, the invention features a method of examining skin health in a subject, the method including the steps of: (a) accessing a sample of interstitial fluid from the skin of the subject; and measuring the amount of a skin analyte in the sample.

In one aspect, the invention features a method of diagnosing the skin health in a subject, the method including the steps of: (a) accessing a sample of interstitial fluid from the skin of the subject; (b) measuring the amount of a skin analyte in the sample; and (c) comparing the amount of the skin analyte to a reference standard.

A method of treating the skin of a subject, the method including the steps of: (a) accessing a sample of interstitial fluid from the skin of the subject; (b) measuring the amount of a skin analyte in the sample; and (c) applying a skin care product to the subject to alter the amount of the skin analyte in the skin of the subject.

A method of distributing a skin care product to a subject, the method including the steps of: (a) obtaining a sample of interstitial fluid from the skin of the subject; (b) measuring the amount of a skin analyte in the sample; and (c) distributing a skin care product to the subject to alter the amount of the skin analyte in the skin of the subject.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

Definitions

What is meant by "examining skin health" is obtaining information regarding the current biological condition of the skin. Such information, for example, may provide insight into the current health of the skin (e.g., to determine whether certain cosmetic or pharmaceutical skin treatments are necessary) as well as provide insight regarding the response of the skin to external trauma or treatment. In one embodiment, the information is obtained on a periodic basis, e.g., once a year, once a month, once a week, or once a day, to continually monitor skin health.

What is meant by "skin analyte" is a chemical entity present in the interstitial fluid of the skin that either participates in the biological processes of the skin or is a product of such processes. In one embodiment, the skin analyte is an endogenous substance. In one embodiment, the skin analyte is an exogenous substance that entered the skin intentionally or unintentionally, which may exert desirable or undesirable biological effects on the skin.

Interstitial Fluid

The present invention relates to a method of examining skin health in a subject by obtaining a sample of interstitial fluid from the skin of said subject (e.g., a mammalian subject such as a human). What is meant by "interstitial fluid" is the clear fluid present between the cells in the living epidermis and dermis, which is substantially free of blood cells.

Creation of Openings in the Skin

The epidermis and dermis are protected by the stratum corneum, which is a barrier layer of keratinized skin cells and lipids. Thus, in order to gain access to interstital fluid, one must permeabilize the stratum corneum to access the interstitial fluid from the skin. In one embodiment, the method of obtaining such sample of interstitial fluid comprises creating an opening in the stratum corneum of the skin of said subject and obtaining said sample through the opening. In one embodiment, the opening is also within the epidermis of the subject. Although not preferred, in one embodiment the opening is also within the dermis of said subject. Preferably, the opening results in minimal residual tissue damage in order not to alter the composition of the interstitial fluid. For example, creating a blister on the skin and then sampling the resulting interstitial fluid in the blister is not preferred.

In one embodiment, about 1 to about 1000 openings are created in the skin of the subject, such as about 2 to about 50 openings. In one embodiment, the width of the opening is about 1 to about 500 microns, such as about 50 to about 250 microns. In one embodiment, the depth of the opening is about 50 to about 500 microns, such as about 75 to about 200 microns. The number and size of openings will depend on the subject being treated and the area of skin being analyzed.

In one embodiment, the opening is created by a mechanical device. Examples of such mechanical devices include, but are not limited to, hollow and solid needles, micro styluses, trochars, blades, and lancets. In one embodiment, such devices have an external diameter or width of up to 1 mm, such as bout 10 and about 200 microns. In one embodiment, the mechanical device creates an opening either by piercing or scraping the stratum corneum. Examples of such mechanical devices can be found in PCT Patent Applications Nos. WO 95/10223, WO 98/11937, WO 97/48440, WO 97/10745, WO 97/08987, W098/00193, WO 00/35530, WO 00/74763, WO 00/74764, WO 00/74766, and WO 01/28423; U.S. Pat. Nos. 5,250,023, 5,885,211, and 5,843,114; and Henry et al., Journal of Pharmaceutical Sciences, Vol. 8, p. 922–25 (August, 1998).

In one embodiment, the opening is created by a heating device. Examples of heating devices include, but are not limited to, heated elements (e.g., an ohmic heating element such as a wire heated by electric current), lasers, and focused light beams of multiple wavelengths. In a further embodiment, a dye that exhibits an absorption of light over the emission range of the laser or focused light beam is first applied to the skin such that the dye is heated sufficiently to create the opening. Examples of such heated elements, laser, and focuses light beams are disclosed in U.S. Pat. Nos. 5,885,211, 5,155,992, and 6,056,738; and PCT Patent Application Nos. WO 99/40848, WO 99/27852, WO 99/20181, WO 97/42888, and WO 99/59485.

In one embodiment, a beam of sonic energy is used to create the opening in the stratum corneum. Examples of such sonic devices and/or the use thereof to create openings in the stratum corneum are disclosed in U.S. Pat. Nos. 5,445,611, 5,458,140, and 5,885,211.

In one embodiment, a short pulse of electricity is used to create the opening in the stratum corneum. Examples of such use can be found in U.S. Pat. No. 5,885,211.

In one embodiment, a high pressure jet of a fluid, gas, or particulate is used to create the opening in the stratum corneum. Examples of the use of such high pressure jets can be found in U.S. Pat. No. 5,885,211.

In one embodiment, an electric arc is used to create the pore in the stratum corneum. Examples of such a device and the use of such a device to create an opening in the stratum corneum is disclosed in PCT Patent Application No. WO 01/13989.

In embodiment, electromagnetic radiation is used to disrupt the stratum corneum in order to create openings to access the interstitial fluid. Examples of such uses are set forth in Tope, Dermatol Surg 25:348–52 (1999).

Although not preferred, in one embodiment, a suction blister is created on the skin, and the roof of the blister is pieced or removed to obtain the interstitial fluid within the blister. An example of such a device and the use of this device to so obtain interstitial fluid is disclosed in Evedman, Pharm. Res., 15:6, 883–8 (1998).

Accessing Interstitial Fluid

In one embodiment, a sample of the subject's interstitial fluid is extracted by various means known in the art. Examples include, but are not limited to: a mechanical suction device with the structure similar to a syringe; a manual mechanical suction device using a piston and a series of one-way valves with the working mechanism similar to commercial apparatuses such as MityVac II® vacuum pump (Prism Enterprises, San Antonio, Tex., USA) and Aspivenin® (ASPIR, Sannois, France); a small size motor-driving suction/vacuum pump; a rubber pipeting suction bulb such as Bel-Bulb® Pipettor (Bel-Art Products, Inc., N.J., USA) and Welch® Suction Cup Electrode (Hewlett Packard, Rockville, Md., USA); a pre-manufactured vacuum chamber with the working mechanism similar to the Vacumtainer® (Becton, Dickinson and Company, Franklin Lakes, N.J.); and a battery-driven suction device for cleaning of facial skin pores such as Panasonic EH2591s Pore Cleanser (Matsushita Electric Works, Ltd. Osaka, Japan).

Kneading or vibration or pressure mechanism may be used together with such suction devices to manipulate the skin around the opening to facilitate the collection of the interstitial fluid. Example of such methods can be found in PCT Patent Application Nos. WO 97/428882 and WO97/08987. A method of heating the skin around the opening may also be used, with or without suction, to facilitate the interstitial fluid collection. Such an example can be found in U.S. Pat. No. 6,155,992. Other methods of enhancing the extraction of interstitial fluid include iontophoresis as well as the use of sonic energy and ultrasound. Such an example can be found in PCT Patent Application Nos. WO 00/549, 240 and WO 97/04832, U.S. Pat. No. 6,173,202, and European Patent Application 1,098,589.

To enable a speedy extraction of interstitial fluid with minimal discomfort when a mechanical suction device is used, the suction force may be within the range of 5–75 cm Hg (e.g., 20–60 cm Hg).

Alternative methods for obtaining interstitial fluid include placing on the opening(s) a capillary tube or an absorbent material (e.g., gauze or non-woven pad, sponge, hydrophilic polymers of porous structure). For example, interstitial fluid can be extracted using an osmotic pressure by contacting the skin (e.g., skin in which the stratum corneum has been compromised as stated above) with a hygroscopic material such as glycerin, glycols such as polyethylene glycols and polypropylene glycols, urea, or polyvinylidone. Other examples include inserting an optical fiber within the opening to register light interaction with an analyte. See PCT Patent Application No. WO 99/07277.

In one embodiment, a permeation enhancer is used to enhance the extraction of the interstitial fluid. Examples of permeation enhancers include, but are not limited to, dimethyl sulfoxide, sodium hydroxide, dimethylamino ethanol, butanol, propylene glycol, oleic acid, and azone. Examples of permeation enhancers are disclosed in U.S. Pat. Nos. 5,458,140, 5,445,611, 4,775,361, and 4,863,970.

In one embodiment, the interstitial fluid is collected in the same device that created in the opening in the stratum corneum (e.g., a device that comprises (i) a mechanical device or a heating device to create the opening in the stratum corneum and (ii) a vacuum device to extract a sample of the interstitial fluid). In a further embodiment, the device is further capable of measuring the concentration of the skin analyte(s) in the collected sample as described below (e.g., using a sensor for the analyte).

Analysis of Skin Analytes

After the interstitial fluid has be accessed (e.g., through the opening(s) created in the stratum corneum by one or more of the methods described above), the concentrations of a skin analyte(s) in the interstitial fluid can be measured with standard analytical methods known in the art such as assays based on enzymatic reaction, antibody interaction, ion-selective electrode, oxidation-reduction electrode; infrared (IR), ultraviolet (UV) spectrophotometry, colorimetry, gene array technology, and gene amplification. Examples of such assays are described in "Sensors in Biomedical Applications" by Gabor, Technomic Pub Co, Lancaster, Pa., 2000; and "Novel Approaches in Biosensors and Rapid Diagnostic Assays" edited by Liron et al, Plenum Pub Corp, New York, 2000.

Alternatively, analysis of the biological substances of interest in the interstitial fluid may be performed through the opening created by placing an analytical instrument (e.g., an infrared or ultraviolet spectrophotometer) directly over the opening, without actually extracting the interstitial fluid out of the skin.

The present invention relates to a method of measuring the amount of biochemical component in said sample (herein referred to as a "skin analyte"). The skin analyte is substance which will provide feedback as to the health of the skin, e.g., provide a marker for possible skin disorders such as but not limited to: intrinsic skin aging, wrinkles, acne, photodamage, rosacea, scars, hypertrophic scars, keliods, stretch marks or striae distensiae, psoriasis, nutrient status, anti-oxidant status, energy status, oxygen status, eicosanoid staus, leukotriene status, pruritus, ehlers-danlos syndrome, scleroderma, post inflammatory hyperpigmentation, melasma, alopecia, poikiloderma of civatte, viteligo, skin cancers, skin dyschromas or blotchy pigmentation.

In one embodiment, the skin analyte is predominantly found in the skin. Examples of such skin analytes include, but are not limited to, enzymes such as the family of matrix metalloproteinases such as MMP 1 through MMP-13, stromolysin, elastase, glucosylceramide synthetase, and glutathione peroxidase; antibodies that demonstrate status of a skin disorder; macromolecules such as the collagen family of proteins such as collagen I through collagen XVIII, elastin, keratins, and glycosaminoglycans; the integrin family of matrix receptors such as integrins type alpha 2 through 10 and integrins type beta 1 through 8; cytokines such as insulin-like growth factors such as IGF-1 and tissue inhibitor of matrix proteinases; and derivatives thereof.

Other skin analytes include, but are not limited to, enzymes such as B-galactosidase, ALA and ASP transferase, protein kinase C, NO synthetase, ornithine decarboxylase, ubiquitin-conjugating enzymes, phosolipid hydroperoxide, death associated protein kinase, DAP kinase or other serine-threonine kinases involved in cellular apoptosis, and superoxide dismutase; macromolecules such as hylauronic acid, fibronectin, fibrin, basement membrane components including laminin and type IV collagen; cytokines such as platelet derived growth factor, keratinocyte growth factor, epidermal growth factor, fibroblast growth factors, connective tissue growth factor, transforming growth factor beta such as TGF-β 1 through TGF-β 3, Vascular endothelial growth factor, growth hormone, tissue plasminogen activator or plasminogen activator tissue type or urokinase type, tissue plasimogen activator inhibitor, plamasinogen activator inhibitor type I and II, interleukins such as IL-1α, heat shock proteins, thrombospodin, the family of Complement glycoproteins, and interferons; immunoglobulins such as IG-G, IG-A, and IG-E; inflammatory mediators such as prostaglandins, dihydroxy testosterone, leukotrienes, histamine, substance P, and tumor necrosis factor; hormones such as estrogens, phytoestrogens, testosterones such as dihydroxytestosterone, melanocyte stimulating factor, adrenocorticotropic hormone, and urocortin; antioxidants such as vitamins (e.g., vitamins A, Bs, C, and E), polyphenols, and leukopene; coenzyme Q-10; and CEHC, and derivatives thereof.

In one embodiment, the concentration of such skin analyte is compared to a reference standard for such skin analyte, e.g., to determine whether such concentrations are above or below normal concentration levels for such subject. In one embodiment, such determination may indicate whether such patient is suffering or at risk for suffering from a skin disorder. In one embodiment, such determination may indicate whether current treatment of a skin disorder is effective, or it may indicate whether a future treatment regimen may be effective.

Diagnosis of Subject

In one embodiment, the subject is a mammal such as a human. The method of the present invention may be used on both healthy subjects (e.g., to ensure their skin health) as well as subjects who are inflicted at various stages with a skin disorder, including but not limited to intrinsic skin aging, wrinkles, acne, photodamage, rosacea, scars, hypertrophic scars, keliods, stretch marks or Striae distensae, psoriasis, nutrient status, anti-oxidant status, energy status, oxygen status, eicosanoid staus, leukotriene status, pruritus, ehlers-danlos syndrome, scleroderma, post inflammatory hyperpigmentation, melasma, alopecia, poikiloderma of civatte, viteligo, skin cancers, skin dyschromas, or blotchy pigmentation.

As many skin disorders are not always visibly apparent (e.g., early stage photodamage to the skin), the methods of the present invention provide a means for early diagnosis of such skin disorders. The patient and/or doctor, thus, can then attempt to treat such disorders at an early stage before such disorders are visually manifested. In one embodiment, the method of the present invention may also be used to determine whether a certain skin treatment would be effective or whether a skin treatment is stabilizing, alleviating, and/or curing the skin disorder.

For example, a subject can be analyzed to determine whether it has adequate levels of minoxidil synthase in its skin prior to initiation of treatment with minoxidil. Another example is the use of monoclonal antibodies to TNF-α as a treatment for psoriasis. High levels of TNF-α have been implicated in the presence and severity of psoriatic plaques. Treatment with the monoclonal antibody inhibits the action of TNF-α and results in the resolution of the plaque. Continued measurement of the ratio of TNF-α to MABTNF-α may predict the necessity of treatment in order to maintain the disease in a quiescent state. The use of the present invention would allow measurement of the antigen/antibody level in the skin, which may provide a more accurate assessment of the condition than the same measurement taken from circulating systemic blood.

Thus, such monitoring using the methods of the present invention may decrease the cost, side effects, and inconvenience of a typical timed regimen, thereby, improving the quality of life of the patient.

Skin Care Compositions

Following analysis of the interstitial fluid, a skin care composition can be administered to the subject to address any problems identified following the analysis of the skin analytes. In one embodiment, a skin care product is administered, e.g., by the subject or a doctor, to said subject to alter the amount of said skin analyte in the skin of the subject.

What is meant by a "skin care product" is a topical composition comprising cosmetically active agent. What is meant by a "cosmetically active agent" is a compound (e.g., a synthetic compound or a compound isolated from a natural source) that has a cosmetic or therapeutic effect on the skin, including, but not limiting to, anti-aging agents, lightening agents, darkening agents such as self-tanning agents, anti-acne agents, shine control agents, anti-microbial agents, anti-inflammatory agents, anti-mycotic agents, anti-parasite agents, anti-cancer agents, agents for photodynamic therapy, steroids, external analgesics, sunscreens, photoprotectors, antioxidants, keratolytic agents, detergents/surfactants, moisturizers, nutrients, amino acids, amino acid derivatives, minerals, plant extracts, animal-derived substances, vitamins, energy enhancers, anti-perspiration agents, astringents, deodorants, hair removers, hair growth stimulators, hair growth retarding agents, firming agents, anti-callous agents, and agents for hair, nail, and/or skin conditioning.

In one embodiment, the agent is selected from, but not limited to, the group consisting of hydroxy acids, benzoyl peroxide, sulfur resorcinol, ascorbic acid, D-panthenol, hydroquinone, octyl methoxycinnimate, titanium dioxide, octyl salicylate, homosalate, avobenzone, polyphenolics, carotenoids, free radical scavengers, spin traps, retinoids such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, peptides such as those disclosed in PCT Patent Application No. WO 00/15188, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera and legumes such as soy beans, and derivatives and mixture thereof. The cosmetically active agent will typically be present in the composition of the invention in an amount of from about 0.001% to about 20% by weight of the composition, e.g., about 0.01% to about 10% such as about 0.1% to about 5%.

Example of vitamins include, but are not limited to, vitamin A, vitamin Bs such as vitamin B3, vitamin B5, and vitamin B12, vitamin C, vitamin K, and vitamin E and derivatives thereof.

Examples of hydroxy acids include, but are not limited, to glycolic acid, lactic acid, malic acid, salicylic acid, citric acid, and tartaric acid. See, e.g., European Patent Application No. 273,202.

Examples of antioxidants include but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, glutathione, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their and their derivatives (e.g., genistein and diadzein), extracts containing resveratrol and the like. Examples of such natural extracts include grape seed, green tea, pine bark, and propolis. Other examples of antioxidants may be found on pages 1612–13 of the ICI Handbook.

Various other materials may also be present in the compositions useful in the subject invention. These include humectants, proteins and polypeptides, amino acids, ion conjugated amino acids preservatives and an alkaline agent. Examples of such agents are disclosed in the ICI Handbook, pp. 1650–1667.

The compositions of the present invention may also comprise chelating agents (e.g., EDTA) and preservatives chelating agents are listed in pp. 1626 and 1654–55 of the ICI Handbook. In addition, the topical compositions useful herein can contain conventional cosmetic adjuvants, such as dyes, opacifiers (e.g., titanium dioxide), pigments, and fragrances.

Distribution of Skin Care Products

Skin care products may also be distributed to subjects based upon the knowledge obtained for the measurement of a skin analyte in the subject's interstitial fluid. For example, a skin care product may be distributed to the subject to alter (e.g., increase or decrease) the amount of the skin analyte in the skin of the subject directly or indirectly. Furthermore, a profile of specific analytes in the skin may be more predictive of a disease or traumatic state of the skin that may require a unique combination of ingredients delivered in a specific regimen. Thus, specific skin care products may be distributed to subjects to address the subject's individual needs. As used herein, "distributing a skin care product" includes the giving, selling, as well as providing a prescription, for a skin care product. Thus, retail establishments can use the methods herein to sell skin care products to customers. Doctors, such as dermatologists, can use the methods herein to both diagnose subjects who are suffering, or at risk of suffering, from a skin disorder, and provide the subject with a skin care product or a prescription for a skin care product.

The following is a description of the extraction and analysis of various skin analytes from human subjects. Other methods of the invention can be practiced in an analogous manner by a person ordinary skill in the art.

EXAMPLE 1

The following two clinical studies were conducted to collect interstitial fluid ("ISF") from human subjects for the purpose of measuring various skin analytes contained therein. The skin analytes vitamin C, interluekin -1α ("IL-1A"), and metalloproteinase-1 ("MMP-1") were measured during the first clinical study ("Study 1") while the analytes vitamin C, immunoglobulin E ("IGE"), insulin-like growth factor-1 ("IGF-1")IL-1A, IL-1 receptor antagonist ("IL-1 RA") and MMP-1 were measured in the second clinical study ("Study 2"). It is believed that these skin analytes may be predictive of the level of intrinsic or extrinsic skin aging.

The studies included non-smoking, male and female subjects of good health over the age of 35 years and under the age 55 years with skin type of III or less by the Fitzpatrick Skin classification. Study 1 was conducted with 20 patients during the month of June while Study 2 was conducted with 27 patients during the month of September. Subjects in each study had the ISF removed from skin both on the dorsal arm ("sun-exposed area") and from skin on the buttocks ("sun-protected area"). Patients were also subdivided into groups who took vitamin C supplements (e.g., orally taking multi-vitamins and/or vitamin C). In study 2, subjects were also separated to those who had a high body mass index (BMI>=27) to see if available fluid in the skin made a difference in collection or concentration of recovered analytes.

The stratum corneum of the sites from which the ISF was removed were first opened using a laser device which activates a dye on the skin surface as described in U.S. Pat. No. 5,885,211. The device was obtained from SpectRx Inc. (Norcross, Ga. 30071). The laser made four pores at each collection site. Two collection sites were used in study 1 while four collection sites were used in study 2. These areas were shaven, if necessary, to remove any hair which may interfere with the procedure and then prepped using a skin cleanser prior to poration.

Following poration of the stratum corneum, a hand held vacuum apparatus was attached to the site using an "A" style harvesting head. The head was attached to the skin with a medical grade adhesive. The sample reservoir in the area over the opening was visually monitored to track the ISF flow rate. ISF was collected into thin-walled medical tubing, which allows for visual fluid quantification. The clear plastic tubing also allowed the researcher to visually assess any sign of redness or irritation and the presence of blood.

The ISF collection period lasted between 3 and 6 hours, typically 4 hours. The amount of ISF collected during each of the studies are set forth in Tables 1 and 2, separated by the location of the skin tested. These results indicated that an increase in the number of openings consequently increased the volume of ISF collected as patients in Study 1 received eight openings while those in Study 2 received sixteen openings. Additionally this data suggests that the amount of fluid acquired is site dependent as it was found to be easier to extract fluid from the arm than from the buttock.

TABLE 1

Study 1 Sample Volume of Interstitial Fluid

|  | Sample Volume Arm (uL) | Sample Volume Buttocks (uL) |
|---|---|---|
| Mean | 106.2 | 75.05 |
| Standard Error | 9.16 | 12.79 |
| Median | 100 | 65 |
| Count | 20 | 20 |

TABLE 2

Study 2 Sample Volume of Interstitial Fluid

|  | Sample Volume Arm (uL) | Sample Volume Buttocks (uL) |
|---|---|---|
| Mean | 262 | 252 |
| Standard Error | 23 | 24 |
| Median | 250 | 275 |
| Count | 27 | 27 |

Analysis of the data from study 1 indicates that IL-1A can be measured in as little as 10 microliters of interstitial fluid from skin.

Levels detected corroborate previous findings in the literature suggesting that sun-exposed skin has a lower concentration of 1L-1A than sun protected skin. Furthermore, the levels do not correlate with supplementation or level of Vitamin C. On the other hand, twice as much ISF was necessary to detect levels of MMP-1 due to the lower concentration of the enzyme in skin. Data suggests that it is present and is in a lower amount in sun protected skin of non-supplemented subjects. It can be inferred that levels of MMP may fluctuate due to the degree of photodamage and level of antioxidant present in the skin suggesting that the level of Vitamin C may be a surrogate marker of extrinsic skin aging.

Tables 3–6 report the results from the determination of the concentration of vitamin C in these two studies. Vitamin C was measured using a standard assay described in the Laboratory Procedures Used by the Clinical Chemistry Division, Centers for Disease Control, for the Second Health and Nutrition Examination Survey (HANES II) 1976–1980, published by the U.S. Department of Health and Human Services, Public Health Services, Atlanta, Ga., pp. 17–19 (1979).

The results of Study 1 are depicted in Tables 3 and 4, separated by (i) the location of the skin tested and (ii) whether subjects who took vitamin C supplements.

TABLE 3

Concentration of Vitamin C in Sun Protected Skin ISF (Non-supplemented Vs Supplemented)

|  | Vitamin C, Non-supplemented (Buttocks) (mg/dl) | Vitamin C, Supplemented (Buttocks) (mg/dl) |
|---|---|---|
| Mean | 1.50 | 1.71 |
| Standard Error | 0.19 | 0.22 |
| Median | 1.52 | 1.44 |
| Count | (F = 4, M = 5) | (F = 1, M = 4) |

TABLE 4

Concentration of Vitamin C in Sun Exposed Skin ISF (Non-supplemented Vs Supplemented)

|  | Vitamin C, Non-supplemented (Arm) (mg/dl) | Vitamin C, Supplemented (Arm) (mg/dl) |
|---|---|---|
| Mean | 1.10* | 1.69 |
| Standard Error | 0.09 | 0.23 |
| Median | 1.18 | 1.58 |
| Count | (F = 7, M = 6) | (F = 3, M = 6) |

*$P < 0.05$ Vs Supplemented Arm ISF

These results of Tables 3 and 4 demonstrate that detectable levels of vitamin C can measured from ISF. Also, a significant difference was found between sun exposed skin (arm) depending on supplementation. The results also found that the amount of vitamin C was significantly less in the arm of non-supplemented subjects than in the arm of supplemented subjects, indicating that vitamin C supplements increase the is endogenous concentration of Vitamin C present in ISF.

The results of Study 2, which examined vitamin C concentration as well as other analytes, are set forth in Table 5–10.

TABLE 5

Concentration of Vitamin C in ISF from Subjects Not Taking Oral Vitamin Supplements

|  | Vitamin C, Supplemented (Buttocks) (mg/dl) | Vitamin C, Supplemented (Arm) (mg/dl) | Vitamin C, Supplemented (Serum) (mg/dl) |
|---|---|---|---|
| Mean | 0.59 | 0.59 | 0.72 |
| Standard Error | 0.11 | 0.18 | 0.13 |
| Median | 0.69 | 0.52 | 0.74 |
| Count | 9 | 9 | 9 |

TABLE 6

Concentration of Vitamin C in ISF from Subjects Taking Oral Vitamin Supplements

|  | Vitamin C, Supplemented (Buttocks) (mg/dl) | Vitamin C, Supplemented (Arm) (mg/dl) | Vitamin C, Supplemented (Serum) (mg/dl) |
|---|---|---|---|
| Mean | 1.223 | 1.1326 | 1.558 |
| Standard Error | 0.091 | 0.094 | 0.122 |
| Median | 1.231 | 1.151 | 1.615 |
| Count | 18 | 17 | 18 |

The results of Tables 5 and 6 also indicate that detectable levels of vitamin C were measured in ISF. The results also discovered that the amount of vitamin C in the ISF was not the same as the amount present in serum, thus, indicating that the a serum measurement of vitamin C is not indicative of its concentration within the skin. The amount of vitamin C measured in Study 2 was also different from that measured in Study 1, indicating the possible seasonal effect (e.g., sun exposure) on the concentration of vitamin C in the skin.

The other skin analytes were measured in Study 2 using standard ELISA kits: MMP-1 (ELISA Cat # QIA55, Oncogene Research Products, Cambridge Mass.); Total IgE (ELISA Cat # RE59061, IBL, Hamburg, Germany distributed by KMI Diagnostics); Non Extraction IGF-1 (ELISA Cat # DSL-10-2800, Diagnostics Systems Laboratories, Webster Tex.); IL-1 RA (ELISA Cat # DRA00, R&D Systems, Minneapolis, Minn.); IL-LA (ELISA Cat # EH2IL1A, Pierce/Endogen, Rockford, Ill.). Tables 7–8 reports on the concentration of these analytes.

TABLE 7

Concentration of Skin Markers Collected from Sun-exposed and Sun-protected Areas

|  | Collection Site | | | | | |
|---|---|---|---|---|---|---|
|  | Sun-exposed | | | Sun-protected | | |
|  | N | MEAN | STD | N | MEAN | STD |
| IgE (log) | 21 | 3.01 | 9.65 | 19 | 12.62 | 7.4 |
| IGF-1 | 24 | 77.84 | 29.42 | 20 | 92.73 | 31.97 |
| IL-1A (log) | 26 | 98.59 | 5.68 | 26 | 182.9 | 3.33 |
| IL-1 RA (log) | 27 | 9902 | 1.66 | 27 | 9552 | 1.65 |
| MMP-1 (log) | 25 | 0.62 | 1.79 | 23 | 0.82 | 2.09 |

TABLE 8

Effect of Supplementation on the Concentration of Skin Markers Collected from Sun-exposed and Sun-protected Areas

| Site | Marker | Supplement | | | | | |
|---|---|---|---|---|---|---|---|
|  |  | No | | | Yes | | |
|  |  | N | MEAN | STD | N | MEAN | STD |
| Sun-exposed | Vitamin C | 4 | 0.55 | 0.18 | 23 | 1.00 | 0.55 |
|  | IgE (log) | 4 | 0.37 | 4.89 | 17 | 4.94 | 8.50 |
|  | IGF-1 | 4 | 82.85 | 28.83 | 20 | 76.83 | 30.17 |
|  | IL-1A (log) | 4 | 33.08 | 52.0 | 22 | 120.24 | 2.84 |
|  | IL-1 RA (log) | 4 | 8660 | 1.60 | 23 | 10140 | 1.68 |
|  | MMP-1 (log) | 4 | 0.51 | 1.95 | 21 | 0.64 | 1.78 |
| Sun-protected | Vitamin C | 4 | 0.67 | 0.28 | 23 | 1.00 | 0.45 |
|  | IgE (log) | 2 | 0.49 | 9.47 | 17 | 18.50 | 5.20 |
|  | IGF-1 | 2 | 47.27 | 4.34 | 18 | 97.78 | 29.52 |
|  | IL-1A (log) | 4 | 141.8 | 15.3 | 22 | 191.5 | 2.22 |
|  | IL-1 RA (log) | 4 | 9899 | 1.46 | 23 | 9492 | 1.70 |
|  | MMP-1 (log) | 3 | 0.41 | 3.47 | 20 | 0.91 | 1.85 |
| Serum | Vitamin C | 4 | 0.82 | 0.22 | 23 | 1.36 | 0.63 |

The results of Tables 7 and 8 indicate that detectable levels of vitamin C can be measured in ISF.

The results of Study 2 also indicated that sun-protected area had significantly ($p<0.01$) higher levels of IgE, IL-1A, and MMP-1. Also the results revealed that vitamin C supplement significantly increased the concentration of vitamin C as well as IgE, IL-1A, IL-1 RA, and MMP-1 in ISF. The study also indicated that males have significantly higher concentrations of IgE, IGF-1, and IL-1 RA, and women had significantly higher concentration of IL-1A. The study also indicated that subjects with a high BMI had higher concentration of IgE.

The results of Study 2 also indicated that sun-exposed and sun-protected values were positively correlated for all values except IGF-1 (i.e., as the sun-exposed values increase, in general, the sun-protected values increase as well). Vitamin C levels from the sun-protected area were also positively correlated with age, implying that Vitamin C levels increase as people age in tissues that are not exposed to oxidative stress. The results also indicated that among those subjects who do not supplement, a very strong negative correlation exists between Vitamin C and MMP-1 for both sun-exposed and sun-protected areas (i.e., as Vitamin C goes up, MMP-1 goes down).

EXAMPLE 2

The following clinical study was performed to demonstrate the concept of application of a bioactive material and the subsequent monitoring of the substance thereafter.

The studies included non-smoking, female subjects of good health over the age of 35 years and under the age 55 years with skin type of III or less by the Fitzpatrick Skin classification. Additionally, subjects did not take any vitamin, nutritional or mineral supplement orally or topically. Interstitial fluid was analyzed for Vitamin C in order to identify a specific population of subjects within approximately one standard deviation of the mean of all potential candidates tested. Acceptable subjects were chronologically enrolled in the study following a randomization code describing what treatment would be applied to which dorsal forearm. Treatments included a high and a moderate concentration of Vitamin C in a topical emulsion. These were compared to each other as well as to the emulsion without Vitamin C. The subject applied a blinded emulsion designated by a letter to one dorsal forearm and an alternative emulsion with a different designation to the opposite arm, twice per day, for three weeks. Vitamin C levels were measured from an aliquot of fluid acquired from the skin and the serum. ISF was extracted from the dorsal forearm, volar upper arm, and serum at one week ("Week 2") and three weeks after dosing ("Week 4") and two weeks after the cessation of dosing ("Week 6").

ISF was extracted from both the treatment site (dorsal forearm) as well as an adjacent, untreated site volar upper arm) following one week of therapy and three weeks of therapy. Subjects ended treatment at this point and returned for a final extraction two weeks later.

The ISF was removed using the same procedure described in Example 1 with the device making four pores at each collection site. The ISF collection period lasted between three and six hours, typically four hours. Vitamin C was measured using a standard assay described in the Laboratory Procedures Used by the Clinical Chemistry Division, Centers for Disease Control, for the Second Health and Nutrition Examination Survey (HANES II) 1976–1980, published by the U.S. Department of Health and Human Services, Public Health Services, Atlanta, Ga., pp. 17–19 (1979).

Results presented in Table 9 demonstrate that application of topical Vitamin C in either high dose or moderate dose modulates the level of Vitamin C at the application site in a dose dependent manner that is significantly different than the placebo that did not contain Vitamin C. The effect was maximal at the first week after therapy was initiated in the high dose treatment group and declined at week four. The moderate dose, however, appeared to stabilize at the concentration achieved during the first week. All doses decreased to approximate baseline values two weeks after ending therapy at week six.

TABLE 9

Concentration of Vitamin C (mg/dl ± STE) at the Application Site (dorsal forearm)

| | High Dose | Moderate Dose | Placebo |
|---|---|---|---|
| Baseline | 0.95 ± .09 | 1.01 ± .09 | 0.91 ± .09 |
| Week 2 | 3.32 ± .82 | 2.02 ± .73 | 0.85 ± .20 |
| Week 4 | 2.02 ± .56 | 2.02 ± .89 | 0.89 ± .12 |
| Week 6 | 1.15 ± .11 | 1.14 ± .07 | 1.09 ± .13 |

As shown in Table 10, further inspection of the subjects in the high dose treatment group demonstrated the immense variability of subject responses. Five of the patients could be considered responders to therapy whereas the other five could be considered non-responders to the therapy. This is an unexpected finding highlighting the necessity of monitoring of bioactive molecules in relation to the health of the skin.

TABLE 10

Concentration of Vitamin C (mg/dl) at the Application Site (dorsal forearm) for the High Dose Group

| | Baseline | Week 2 | Week 4 | Week 6 |
|---|---|---|---|---|
| 1 | 0.94 | 1.55 | 1.73 | 1.57 |
| 2 | 1.1 | 1.43 | 1.42 | 1.22 |

TABLE 10-continued

Concentration of Vitamin C (mg/dl) at the Application Site (dorsal forearm) for the High Dose Group

| | Baseline | Week 2 | Week 4 | Week 6 |
|---|---|---|---|---|
| 3 | 1.19 | 8.32 | 1.3 | 1.32 |
| 4 | 1.08 | 5.53 | 3.55 | 1.1 |
| 5 | 0.37 | 5.71 | 5.92 | 0.38 |
| 6 | 1.15 | 0.95 | 1.37 | 1.24 |
| 7 | 0.66 | 0.58 | NA | 1.21 |
| 8 | 1.14 | 1.33 | 0.71 | 1.14 |
| 9 | 0.68 | 4.05 | 0.62 | 1.16 |
| 10 | 1.22 | 3.78 | 1.53 | NA |

The results in Table 11 illustrate that treatment with a topical application at one area of the body does not influence either levels at an adjacent, untreated site or the serum, suggesting that it is a treatment specific response at the doses tested.

TABLE 11

Concentration of Vitamin C (mg/dl ± STE) for High Dose Group

| Location | Baseline | Week 2 | Week 4 | Week 6 |
|---|---|---|---|---|
| Serum | 0.69 ± 0.08 | 0.66 ± 0.12 | 0.75 ± 0.15 | 1.17 ± 0.11 |
| Adjacent Site (UV) | ND | 0.85 ± 0.12 | 0.90 ± 0.12 | 1.07 ± 0.11 |
| Treatment Site (LD) | 0.95 ± 0.09 | 3.32 ± 0.82 | 2.02 ± 0.56 | 1.15 ± 0.11 |

The results of this study suggest that application of a biologically molecule such as vitamin C can be measured by the methods of the present invention and that due to subject variability this method should be implemented in order to achieve the desired dosing concentration and regimen. The results indicate that using the method of the present invention is the preferred means to establish unique skin responses directly effecting the health of the skin. The prior method of serum monitoring is, as indicated above, ineffective in delineating the biologically pertinent levels as seen below in Table 12. Regardless of the dose of vitamin C applied, the serum level did not respond to topical therapy at the concentrations applied.

TABLE 12

Concentration of Vitamin C (mg/dl ± STE) in the Serum

| Treatment Group | Baseline | week 2 | week 4 | week 6 |
|---|---|---|---|---|
| High Dose | 0.69 ± 0.08 | 0.66 ± 0.12 | 0.75 ± 0.15 | 1.17 ± 0.11 |
| Mid Dose | 0.82 ± 0.08 | 0.76 ± 0.12 | 0.92 ± 0.13 | 1.24 ± 0.07 |
| Placebo | 0.72 ± 0.11 | 0.67 ± 0.17 | 0.86 ± 0.13 | 1.14 ± 0.13 |

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of distributing a skin care product to a subject, said method comprising the steps of:
   (a) obtaining a sample of interstitial fluid from the skin of said subject; and
   (b) measuring the amount of a skin analyte in said sample; and (c) distributing a skin care product to said subject to alter the amount of said skin analyte in the skin of said subject.

2. A method of claim 1, wherein said method comprises creating a opening in the stratum corneum of the skin of said patient and accessing said sample through said opening.

3. A method of claim 2, wherein said opening is created with a needle, a blade, a laser, or an electric arc.

4. A method of claim 3, wherein said opening is created with a laser.

5. A method of claim 4, wherein said method further comprises comparing the amount of said analyte is compared to a reference standard.

6. A method of claim 5, wherein said skin care product comprises a vitamin.

7. A method of claim 4, wherein said skin care product comprises a vitamin.

8. A method of claim 3, wherein said sample is extracted through said opening under negative pressure.

9. A method of claim 8, wherein said skin analyte is a vitamin, an immunoglobulin, an insulin-like growth factor, an interleulin, an interleukin receptor antagonist, or a metalloproteinase.

10. A method of claim 8, wherein said skin analyte is vitamin C.

11. A method of claim 10, wherein said method further comprises comparing the amount of said analyte is compared to a reference standard.

12. A method of claim 11, wherein said skin care product comprises a vitamin.

13. A method of claim 10, wherein said skin care product comprises a vitamin.

14. A method of claim 8, wherein said method further comprises comparing the amount of said analyte is compared to a reference standard.

15. A method of claim 14, wherein said skin care product comprises a vitamin.

16. A method of claim 8, wherein said skin care product comprises a vitamin.

17. A method of claim 2, wherein said sample is extracted through said opening under negative pressure.

18. A method of claim 2, wherein said method further comprises comparing the amount of said analyte is compared to a reference standard.

19. A method of claim 18, wherein said skin care product comprises a vitamin.

20. A method of claim 2, wherein said skin care product comprises a vitamin.

21. A method of claim 1, wherein said skin analyte is a vitamin, an immunoglobulin, an insulin-like growth factor, an interleulin, an interleukin receptor antagonist, or a metalloproteinase.

22. A method of claim 1, wherein said skin analyte is vitamin C.

23. A method of claim 1, wherein said method further comprises comparing the amount of said analyte is compared to a reference standard.

24. A method of claim 23, wherein said skin care product comprises a vitamin.

25. A method of claim 1, wherein said skin care product comprises a vitamin.

* * * * *